United States Patent [19]

Endo et al.

[11] Patent Number: 5,106,955

[45] Date of Patent: Apr. 21, 1992

[54] PROCESS FOR PREPARATION OF ANTIBODY CONJUGATES

[75] Inventors: Noriaki Endo, Kokubunji; Yumiko Takeda, Tokorozawa; Yoshinori Kato, Hino; Takeshi Hara, Hachiooji, all of Japan

[73] Assignee: Teijin Limited, Osaka, Japan

[21] Appl. No.: 304,987

[22] PCT Filed: Mar. 17, 1988

[86] PCT No.: PCT/JP88/00279

§ 371 Date: Nov. 23, 1988

§ 102(e) Date: Nov. 23, 1988

[87] PCT Pub. No.: WO88/07553

PCT Pub. Date: Oct. 6, 1988

[30] Foreign Application Priority Data

Mar. 26, 1987 [JP] Japan .................. 62-70429

[51] Int. Cl.$^5$ ............................ C07K 17/02
[52] U.S. Cl. .................. 530/391.1; 530/402; 530/403; 530/404; 530/405; 530/406; 530/408; 530/409; 530/410; 530/391.3; 530/391.7
[58] Field of Search ............... 530/389, 390, 391, 405, 530/409, 402, 403, 404, 406, 408, 410

[56] References Cited

U.S. PATENT DOCUMENTS 4,671,958 6/1987 Rodwell et al. ............... 424/85.91

FOREIGN PATENT DOCUMENTS 88695 9/1983 European Pat. Off. .

OTHER PUBLICATIONS

Blair et al., (1983) J. Immunol. Methods 59:129–143.
Endo et al., (1981) J. Immunol. Methods 104:253–258.
Gibbons et al., (1970) Brochem J. 116:843–849.
Keller et al. (1975) Helvetica Chiahaica Acta 58, Fasc 2-Nr62-63:531–541.
Chemical Abstracts, vol. 108, No. 5, Feb. 1, 1988, p. 480, abstract no. 36079V, Columbus, Ohio, US; E. Noriaki et al. and J. Immunol. Methods, 1987, 104(1–2), 253–258.

*Primary Examiner*—Christine Nucker
*Assistant Examiner*—Kay Kim
*Attorney, Agent, or Firm*—Sughrue, Mion, Zinn, Macpeak & Seas

[57] ABSTRACT

A process for production of antibody conjugates which comprises modification of a part of the amino groups in an antibody or its fragment whose antigen-binding activity is lowered by the modification of its amino groups, with a reversible modifier for protein amino groups, reaction of the antibody or its fragment with a substance bearing a group reactive with the amino group and removal of the residues of the reversible modifier from the amino groups and, when necessary, the residues of the substance bearing a group reactive with the amino group in case they are introduced onto groups other than amino groups. The process according to the present invention gives antibody conjugates with retention of antigen-binding activity and these conjugates have a possibility of being used in affinity chromatography or as a diagnostic agent or a drug for cancer therapy.

8 Claims, No Drawings

PROCESS FOR PREPARATION OF ANTIBODY CONJUGATES

TECHNICAL FIELD

The present invention relates to a process for production of antibody conjugates from an antibody and a specific compound. Particularly, the present invention relates to a process for production of antibody conjugates by binding a compound having a specific function to an antibody at its amino group with retention of the antigen-binding activity of the antibody.

BACKGROUND OF THE ART

Conjugates resulting from covalent modification of an antibody which can specifically bind to its antigen, at its amino groups with a variety of substances have been used over a wide range of application. For example, a conjugate of a specific antibody and an insoluble support is used in affinity chromatography to isolate a specific substance from its mixture. Another conjugate of an antibody with specificity to a certain tissue in vivo, for example, to a malignant tumor, and a radioactive isotope can accumulate the radioactivity on the tumors to enable diagnostic imaging of cancers. In addition, conjugates of antibodies and biologically active substances can be medicines with high selectivity. For example, a conjugate of an antitumor antibody and an antitumor substance or other cytotoxic substances can act on the tumor with high selectivity as a therapeutic agent. Conjugates of a fluorescent substance or an enzyme with an antibody can be used as an immunological or biochemical reagent or diagnostic agent. Further, new types of conjugates will be created in compliance with future needs.

One of the essential requisites common to the production of these conjugates is that the process can allow a required substance to bind to the antibody satisfactorily with retention of the original function of the antibody to bind to the antigen specifically.

One of the most widely used methods is to bond a substance to an antibody at an amino group (contained in lysine and the N-terminal amino acid) or a carboxyl group (contained in glutamic acid and aspartic acid) in the amino acids constituting the antibody. Particularly, the binding at the amino group has been widely utilized. For example, the conjugate of an antibody with an insoluble support for the separation and purification of a certain substance by affinity chromatography is prepared by introducing a group reactive with the amino groups, namely epoxy, activated carboxylic acid ester, acid azide, or bromoacetyl group or an activated group derived from cyanogen bromide into the support, then binding an antibody to the support at its amino group [see Affinity Chromatography: pages 19 and 87, edited by Makoto Yamazaki, Shinichi Ishii and Koichi Iwai, published by Kodansha (Tokyo), 1975]. Another conjugate of a radioactive substance with an antibody is formed by reaction between a compound bearing an activated carboxylic acid ester group and an antibody at the latter's amino groups, for example, by reaction between an antibody and Bolton-Hunter reagent, a reagent for introduction of radioactive iodine [see A. E. Bolton and W. M. Hunter; Biochem. J. 133, 529-539 (1973)], or by binding such a type of chelating agent as typified by diethylenetriaminepentaacetic acid (abbreviated to DTPA) at its carboxyl group to an antibody at its amino group followed by chelating a radioactive metal exemplified by $^{111}$In [see B. A. Khaw, J. T. Fallon, H. W. Strauss, E. Haber; Science, 209, 295 (1980)]. Further, conjugates of an antibody and a biologically active substance are also formed by binding the substance at its carboxyl group to the antibody at its amino group, as exemplified by conjugation of methotrexate, an antitumor agent [see P. N. Kulkarni, A. H. Blair, T. I. Ghose; Cancer Res., 41, 2700-2706 (1981)]. Conjugates of an antibody and ricin A chain are prepared, as described by K. A. Krolick, C. Villemez, P. Isakson, J. W. Uhr, and E. S. Vitetta [Proc. Natl. Acad. Sci. U.S.A.; 77, 5719-5423 (1980)], by reaction of N-succinimidyl 3-(2-pyridylthio)propionate, a crosslinking agent for introduction of an activated disulfide group with an antibody at its amino group followed by reaction of a thiol group which is contained in ricin A chain with the activated disulfide group.

A variety of conventional production processes for conjugates, however, have a critical disadvantage common to them. It is the fact that any amino groups, whether they are involved in binding of the antibody to the antigen or not, are unselectively employed, when substances are linked to an antibody at one or more amino groups among a number of amino groups present in the antibody protein. Consequently, in case that the amino groups that are involved in the binding to the antigen are more reactive than others, they are readily modified chemically. For example, when a conjugate was formed by reaction of a monoclonal antibody 225.28S against a high-molecular-weight antigen on melanoma cell membranes, with an equimolar amount of an intramolecular acid anhydride of a chelating reagent, DTPA, the antigen-binding activity of the conjugate was found to reduce to about half that of the original antibody [see R. A. Fawaaz, T. S. T. Wang, A. Estabrook, J. M. Rosen, M. A. Hardy, P. O. Alderson. S. C. Srivastava, P. Richards, and S. Ferrone; J. Nuclear Medicine, 26, 488-492 (1985)].

DISCLOSURE OF THE INVENTION

The present inventors have made intense study to develop a widely applicable process for production of antibody conjugates without the above-described disadvantage which conventional processes have not been able to avoid. Thus, the present inventors have worked out a process for production of antibody conjugates which is based on protection, with a reversible modifer, of one or more amino groups including those involved in the activity of an antibody to bind to the antigen, and observed that the conjugates prepared through this protection adequately maintain their antigen-binding activity, even in such conjugate combinations as a decrease in the activity was caused in the conventional processes, thus reaching the present invention.

In other words, the present invention is a process for production of antibody conjugates which comprises modification of a part of the amino groups in an antibody or its fragment whose antigen-binding activity is lowered by modification of the amino groups, with a reversible modifier for protein amino groups, reaction of the protected antibody or its fragment with a substance bearing a group reactive with the amino group, and removal of the residues of the reversible modifier from the amino group and, when necessary, the residues of the substance bearing a group reactive with the amino group in case they are introduced onto groups other than amino groups.

THE OPTIMAL EMBODIMENT FOR THE PRESENT INVENTION

In the present invention, the antibodies whose antigen-binding activity is reduced by modification of their amino groups may have specificity to any types of antigens and haptens. For example, antibodies against cancers, bacteria, viruses, fungi, mycoplasmas or parasites, antibodies against pathogenic substances and tumor-associated substances, antibodies against tumor-associated antigens, cell differentiation antigens, and histocompatibility antigens, antibodies against other cell membrane antigens, and antibodies against toxins, enzymes, allergens, hormones, drugs, and other biologically active substances can be used. Further, the present invention can be applied to both polyclonal antibodies which are produced by immunizing animals with antigens or haptens and monoclonal antibodies which are prepared through cell fusion or through transformation of antibody-producing cells with EB virus. Monoclonal antibodies have an advantage that high-purity antibodies with clear specificity to a variety of antigens can be obtained in large amounts.

The present invention can be applied to antibodies in any classes and subclasses. In other words, antibodies have class of IgG, IgA, IgM, IgD, and IgE, and IgG has subclass of IgG1, IgG2a, IgG2b, and IgG3; IgA, IgA1 and IgA2; and IgM, IgM1 and IgM2, and antibodies in any class and subclass can be used as an antibody for the present invention. The antibodies may be used in the form of the whole molecule, and also they can be used in the form of fragments containing the antigen-binding sites. As such a fragment, is cited, for example, IgMs, a monomer of IgM antibody, a monomer of IgA, the divalent fragment F(ab')$_2$ obtained by hydrolysis of an antibody molecule with pepsin or the monovalent fragment: Fab obtained by hydrolysis with papain.

In the present invention, a reversible modifier for amino groups of protein may be any chemical compounds, as long as they chemically modify the amino groups which are deeply involved in binding of an antibody or its fragment to the antigen (the covalent binding of the residue of the reversible modifier), then the residues of the modifier can be removed from the product, directly after a substance bearing a group reactive with the amino group is allowed to react with the antibody or its fragment or after the product is further subjected to other chemical reactions, to regenerate the amino groups reversibly. As such reversible modifiers for protein amino groups, are cited substituted or unsubstituted maleic anhydride, substituted or unsubstituted succinic anhydride, reactive derivatives of polyhalogenated carboxylic acids, diketene, 2-hydroxyacetaldehyde and so on. For example, substituted and unsubstituted maleic anhydride are maleic anhydride

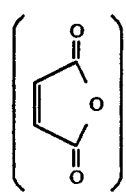

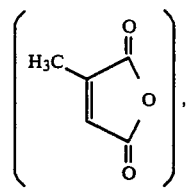

2,3-dimethylmaleic anhydride

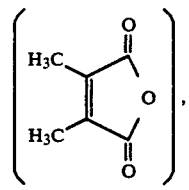

cis-aconitic anhydride

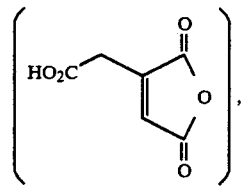

while substituted or unsubstituted succinic anhydrides are tetrafluorosuccinic anhydride

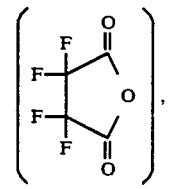

exo-cis-3,6-endoxo-Δ$^4$-tetrahydrophthalic anhydride

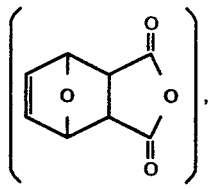

exo-cis-3,6-endoxohexahydrophthalic anhydride

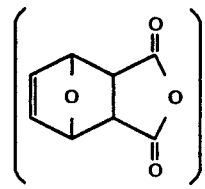

An example of the reactive derivatives of polyhalogenated carboxylic acids is trifluoracetic anhydride.

The substances bearing a group reactive the amino group according to the present invention may be any substance, as long as they are substances which need to be introduced into the antibody or its fragment without significant damage on antigen-binding activity and bear a group reactive with the amino group. A wide range of substances are included, e.g., crosslinking agents, biologically active substances, chelating agents, radioactive substances, fluorescent substances or insoluble supports.

As biologically active substances bearing a group reactive with the amino group, are cited cytotoxic substances, antitumor substances, antibacterials, antivirals, antifungals, antimycoplasmics, antiparasitics, hormones or enzymes. The cytotoxic substances mean here the substances that manifest cytotoxic effect by themselves or reveal the effect, when they are introduced into cells by aid of other substances, for example, a chelating agent with a radioactive isotope emitting alpha-rays or beta-rays bound thereto by chelate bonds, toxins or their fragments having an enzymatic activity.

As such substances bearing a group reactive with the amino group, are particularly preferred substances having an activated carboxyl group as the group reactive with the amino group, and as examples of such antitumor substances, are cited derivatives, having an activated carboxyl group, of compounds shown by the following chemical formulas.

Nitrosourea derivative;

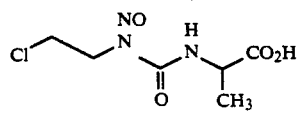

Chlorambucil;

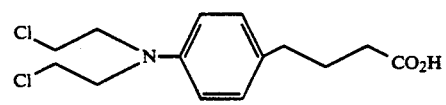

Methotrexate;

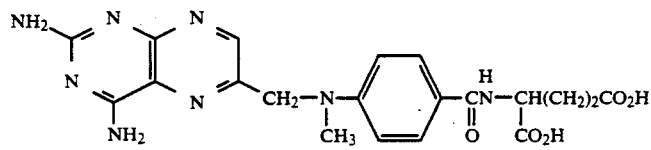

Mitomycin derivative;

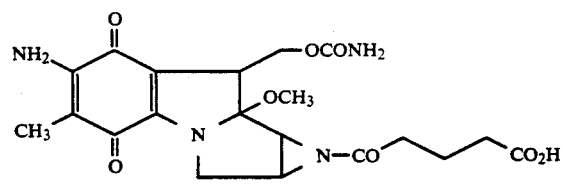

Actinomycin-D oxazinone derivative;

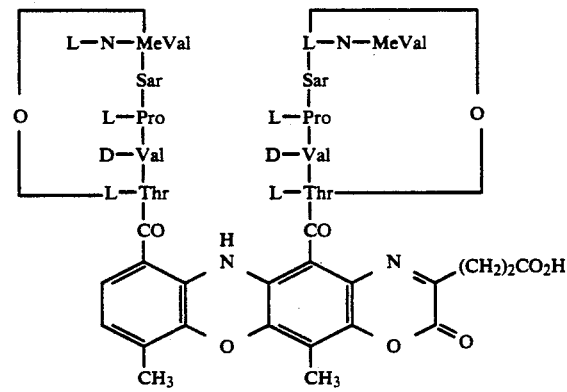

Vinblastine derivative;

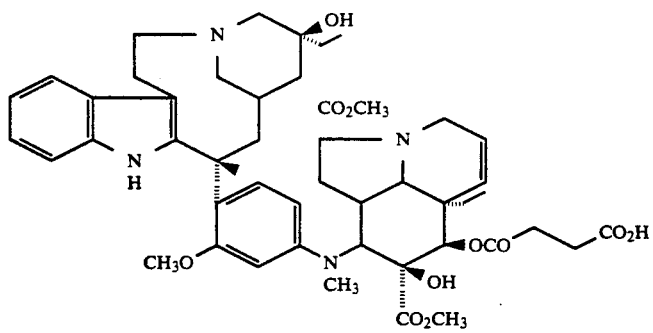

Further, as the chelating agents, are cited derivatives, activated at the carboxyl group, of compounds shown by the following chemical formulas:

Diethylenetriaminepentaacetic acid;

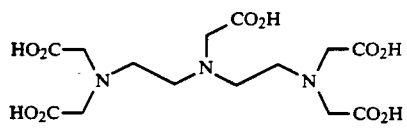

Tris(carboxymethyl)amine,

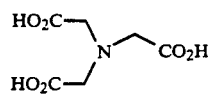

The activated carboxyl groups are, for example, active esters, active amides, acid azides, or acid anhydrides, and alcohol residues forming active esters are, for example, 2,4-dinitrophenoxy,

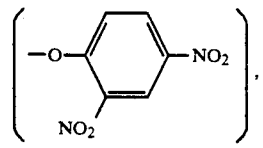

N-succinimidyloxy

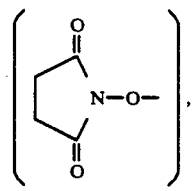

N-5-norbornene-2,3-dicarboxyimidyloxy

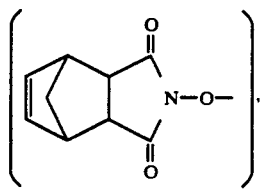

while amine residues forming active amides are, for example,

N-imidazolyl 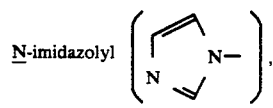,

The acid anhydride group may be a mixed acid anhydride with another acid or may be an intramolecular anhydride if the compound has two carboxyl groups in suitable positions for forming an anhydride group in the molecule. As examples of these acid anhydride groups, are cited following acid anhydrides of chelating agents:

Diethylenetriaminepentaacetic acid derivatives;

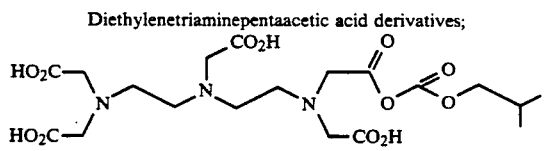

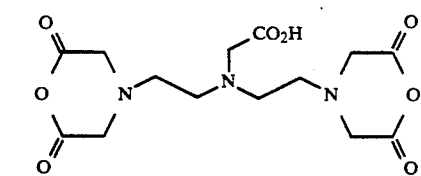

2,6-Dioxo-N-(carboxymethyl)morpholine;

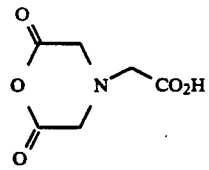

Since the carboxyl group can form an amide bond by condensation with an amino group in the presence of a condensing agent, for example, dicyclohexylcarbodiimide, the above-cited compounds bearing carboxyl groups are, as such, the substances bearing a group reactive with the amino group according to the present invention and, in addition, the reactive intermediates resulting from the reaction of the compounds bearing carboxyl groups with, for example the condensing agent dicyclohexylcarbodiimide (the intermediates are represented by the following formula, when the compounds bearing carboxyl groups are given as R-COOH:

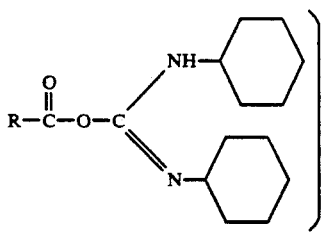

are also included in the compounds bearing an activated carboxyl group according to the present invention.

The reversible modifiers for amino groups which are used in the present invention, namely substituted or unsubstituted maleic anhydride such as maleic anhydride, citraconic anhydride, 2,3-dimethylmaleic anhydride, cis-aconitic anhydride; substituted or unsubstituted succinic anhydride such as tetrafluorosuccinic anhydride, exo-cis-3,6-endoxo-$\Delta^4$-tetrahydrophthalic anhydride, exo-cis-3,6-endoxohexahydrophthalic anhydride; reactive derivatives of polyhalogenated carboxylic acid such as trifluoracetic anhydride, diketene or 2-hydroxyacetaldehyde are commercially available as an industry product. Further, the compounds bearing a group reactive with the amino group to be used as a starting material in the present invention and to be bound to an antibody are selected from a variety of substances, such as crosslinking agents, biologically active substances, chelating agents, radioactive substances, fluorescent substances or insoluble supports and they are available industrially as useful substances or they are obtained by processing substances available industrially so that they can be conveniently used to bind to an antibody by reacting at the amino groups of the antibody.

The process according to the present invention is carried out, in general, through the continuous operations including the following three-step reactions:

(1) protection of the amino groups of an antibody or its fragment with a reversible modifier for protein amino groups;

(2) connection of a compound bearing a group reactive with the amino group to the antibody or its fragment in which a part of the amino groups have been protected, and further chemical processing of the product, when necessary, and (3) removal of the residual groups of the reversible modifier and the residues of the substance bearing a group reactive with the amino group in case the substance has additionally reacted with groups other than amino groups and its residues have been introduced. In the first-step reaction, the amount of the reversibly modifier for protein amino groups depends on the antibody and/or the modifier employed, and preferably ranges from 1 to 500-fold that of the antibody or its fragment on molar basis. The reaction is conducted in such mild conditions as the antigen-binding activity and protein properties of the antibody are not affected, preferably at a pH of 4 to 10 and reaction temperature of $-4°$ C. to $35°$ C. When a substituted or unsubstituted maleic anhydride is used as a reversible modifier, the reaction is preferably effected under weak alkaline conditions of pH 8 to 10, while pH 7 to 9 is preferred, when trifluoracetic anhydride, a reactive derivative of a polyhalogenated carboxylic acid is used. Further, in case of diketene or 2-hydroxyacetaldehyde, the reaction is preferably carried out at pH 4 to 9. The reaction time is generally 10 minutes to 24 hours, but the reaction finishes in 30 minutes to 5 hours in most cases. The antibody bearing amino groups protected with a reversible modifier is subjected to the next-step reaction, after purification or directly in the form of the reaction mixture. The latter operation is employed, when the reversible modifier disappears from the reaction system after a certain time by hydrolysis. Generally, acid anhydrides such as maleic anhydride are in this category. When necessary, the product is purified by a simple procedure with a gel filtration column filled with Sephadex G-25 or by dialysis at a temperature of 4° C. or below.

In the second step, namely the binding of a compound bearing a group reactive with the amino group to an antibody or its fragment in which a part of the amino groups are protected and the following chemical processing of the product, when necessary, the binding reaction is preferably carried out under such conditions as the antibody is not damaged, namely in a pH range from 4 to 10 at a reaction temperature from $-4°$ C. to $35°$ C. It is undesirable that the reaction is effected under such conditions as the release of the residual groups of the modifier is induced. In other words, the reaction with an antibody modified with a substituted or unsubstituted maleic anhydride, for example, exo-cis-3,6-endoxo-$\Delta^4$-tetrahydrophthalic anhydride or exo-cis-3,6-endoxohexahydrophthalic anhydride is preferably conducted in an alkaline solution of pH 7 to 10, while the reaction with an antibody modified with tetrafluorosuccinic anhydride, trifluoracetic anhydride or diketene is preferably carried out at pH 4 to 8.

Similar reaction conditions are applied, too, when the substance bonded to the antibody is further processed. In case of treatment of the antibody modified with 2-hydroxyacetaldehyde, periodic acid must not be employed, when the protection of the amino groups needs to be maintained.

The amount of the compound bearing a group reactive with the amino group depends on the properties of the compound, but is preferably 1 to 100 times the amount of the antibody or its fragment on molar basis. When the compound is sparingly soluble in water, its binding to the antibody in a large amount sometimes makes the antibody insoluble. In this case, the amount of the compound used for the reaction should be limited. But, this does not apply to the case where the substance is originally used as an insoluble substance like an insoluble gel.

In case that the compound bearing a group reactive with the amino group is a crosslinking agent, after the compound has been bonded to an antibody or its fragment, a further processing like binding of a compound bearing a group reactive with the crosslinking group to the residual group of the crosslinking agent introduced into the antibody or its fragment can be carried out. The desirable reaction conditions in this case are similar to those described above.

The reaction to remove the residues of the reversible modifier from the amino groups and to remove, when necessary, residues of the substance bearing a group reactive with the amino group in case they are introduced onto groups other than amino groups can be carried out after the product of the previous step has been purified, but the operation is carried out, in many cases, directly without purification. When purification is conducted, it can be done by gel filtration or ion-exchange column chromatography or by dialysis.

When the residues of the reversible modifier for amino groups and, when necessary, the residues of the substance bearing a group reactive with the amino group introduced onto the groups other than amino groups are removed, the reversible amino group modifier, if it remains unreacted in the system, may be inactivated with an amino compound such as lysine or 2-aminoethanol, if needed, before the reaction for the removal.

Either the removal of the residues of the reversible modifier from amino groups or the removal of the residues of the substance bearing a group reactive with the amino group introduced onto the groups other than amino groups may be conducted prior to the other, or both operations may be conducted simultaneously. In some reactions, conditions which can remove either of the two kinds of the residues can remove the other or a part of them.

The preferred conditions for removing the residues of the reversible modifier from the amino groups in an antibody are discussed here. Maleyl, exo-cis-3,6-endoxo-$\Delta^4$-tetrahydrophthalyl, exo-cis-3,6-endoxohexahydrophthalyl groups are preferably removed by treatment under weak acidic to nearly neutral conditions of pH 4 to 8. The reaction temperature is preferably $-4°$ to $35°$ C. and the reaction time is usually 0.5 to 96 hours. Further, tetrafluorosuccinyl, trifluoroacetyl or acetoacetyl groups are preferably removed under weakly alkaline conditions of pH 8 to 10. Further, a basic substance such as hydroxylamine and morpholine may be added as an auxiliary agent at 10 mM to 100 mM concentration to promote the removal reaction. The reaction temperature is preferably $-4°$ C. to $35°$ C., and the reaction time is usually 0.5 to 96 hours. 2-hydroxyethyl groups can be eliminated by action of 1 to 10 mM periodic acid.

The activated groups of carboxyl groups are highly reactive with amino groups and are reactive with hydroxyl groups in serine, threonine or saccharides as well. Accordingly, in case that the substance bearing a group reactive with the amino group is a compound bearing an activated group of the carboxyl group, it reacts with serine, threonine and saccharide residues of the antibody, when they are allowed to react with an antibody or its fragment in which a part of the amino groups are modified with the reversible modifier for protein amino groups. This is the case where the residues of a substance bearing a group reactive with the amino groups have been introduced into groups other than amino groups. The residues of the substance bearing a group reactive with the amino group which have been introduced onto groups other than amino groups are removed, when needed. In the case, as exemplified above, where an activated group of the carboxyl group has reacted with serine or threonine residues or saccharides in an antibody to introduce the residues of the substance bearing a group reactive with the amino group into the antibody through the ester bond, the residues can be eliminated by hydrolysis of the ester bonds under weak alkaline or acidic conditions or by cleavage of the bonds with an amine such as hydroxylamine. The cleavage reaction can be conducted, for example, by treatment with 0.01 to 1.0-M hydroxylamine at 0° to 40° C. and at pH 6 to 10. The time required is 1 hour to 5 days. In some cases, the residues of reversible amino group modifiers are partially or wholly released by this treatment and, in such cases, the process is preferably combined with the removal process for the residues of the amino group modifiers.

In the purification of the antibody conjugates prepared as above, low-molecular-weight substances can be removed in a usual manner, for example, by dialysis, gel filtration, ammonium sulfate precipitation or, ethanol precipitation. When the conjugates are insoluble, simple filtration, rinsing or the like can be employed. High-molecular-weight substances can be removed in a usual manner, for example, by gel filtration, ion-exchange chromatography or isoelectric point precipitation.

The present invention will be illustrated in more detail by the following examples, but it will not be limited to these examples, as a matter of course.

EXAMPLE 1

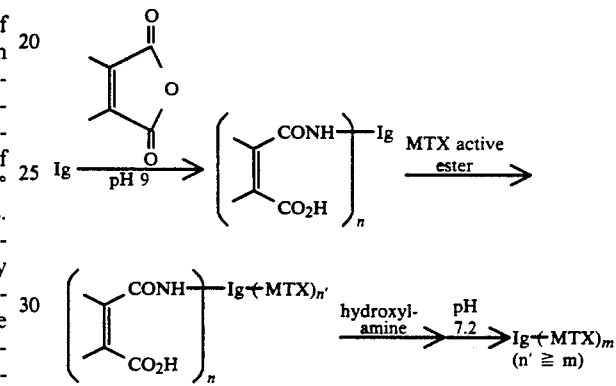

1-1: Preparation of Conjugates

To 1.7 ml of a solution of monoclonal antibody 96.5 against human melanoma (12.0 mg) in 70 mM borate buffer (pH 8.8) was added 20 μl of a 0.2-M dimethylmaleic anhydride solution in DMF under cooling with ice-water and the mixture was stirred for 30 minutes to effect the reaction. During the reaction, 0.1M aqueous sodium hydroxide was added dropwise to keep the pH of the reaction mixture at 8.5 to 9.0. Then, 52 μl of a 30.5-mM solution of N-hydroxysuccinimide ester of methotrexate (abbreviated as MTX hereinafter) [which was prepared by the process described by P. Kulkarni et al; Cancer Research, 41, 2700–2706 (1981) with some modification and improvement] in DMF was added, and the reaction was allowed to proceed for 4 hours.

Then, 120 μl of a 0.4M-glycine solution in 0.1 borate buffer (pH 8.5) was added and the mixture was stirred at 4° C. for 1 hour to stop the reaction. Further, 180 μl of an 1.1M-hydroxylamine solution in 0.1M borate buffer (pH 9.0) was added and the mixture was allowed to stand at 4° C. for 3 days. The reaction mixture was dialyzed against 0.02M phosphate-buffer-0.14M sodium chloride (pH 7.2) at 4° C. for 40 hours to remove the dimethylmaleyl groups and the MTX bound to the hydroxyl groups in the antibody molecule to give 2.2 ml of a solution of the desired conjugate. Further, the reaction ratio between the antibody and dimethylmaleic anhydride and the ratio between the antibody and MTX N-hydroxysuccinimide ester were altered to prepare two antibody-MTX conjugates. Table 1 shows the relationship between the reaction molar ratios of dimethylmaleic anhydride to the antibody and of MTX N-hydroxysuccinimide ester to the antibody and the average number of MTX molecules bound to one molecule of the antibody. The average number of MTX molecules bound to one antibody molecule (molar ratio) was determined by the method described in 1 - 2.

TABLE 1

| DMA*/antibody (molar reaction ratio) | MTX-OSu**/antibody (molar reaction ratio) | MTX/antibody (molar binding ratio) |
| --- | --- | --- |
| 50 | 20 | 4.1 |
| 100 | 40 | 5.8 |
| 200 | 50 | 5.0 |

Notes:
*DMA = dimethylmaleic anhydride
**MTX-OSu = MTX N-hydroxysuccinimide ester

1-2: Determination of Conjugates

A portion of the conjugate solutions prepared in 1-1 was used to measure absorbances at 280 nm and at 372 nm and the antibody protein and MTX in the conjugates were determined from individual measurements. It has been confirmed in experiments that the absorbance at 280 nm due to MTX is 2.52 times that at 372 nm due to MTX and the absorbance at 280 nm due to immunoglobulin was obtained by subtracting the absorbance due to MTX from the absorbance of the conjugate at 280 nm to quantify the antibody protein. The results are given in Table 1.

1-3: Preparation of Conjugates of an Antibody and MTX Without Partial Protection of Protein Amino Groups With a Reversible Modifer for the Sake of Comparison To 0.3 ml of a solution of 96.5 antibody (3.0 mg) in 0.1M borate buffer (pH 8.5) was added 5 μl of a 30.6-mM solution of MTX N-hydroxysuccinimide ester in DMF (the same solution as in Example 1-1) to effect the reaction for 4 hours. Then, the reaction was stopped by adding 12 μl of a 0.4-M glycine solution in 0.1M borate buffer (pH 8.5) and stirring the mixture at 4° C. for 1 hour. Subsequently, 30 μl of an 1.1M-hydroxylamine solution in 0.1M borate buffer (pH 9.0) was added and the mixture was allowed to stand at 4° C. for 3 days to remove MTX bound to hydroxyl groups in the antibody molecule. The reaction mixture was dialyzed against 0.2M phosphate buffer-0.14M sodium chloride (pH 7.2) at 4° C. for 40 hours to give 0.65 ml of a solution of the desired conjugate. The constitution of the conjugate was determined by the same method as in 1-2 to show that on average, 4.5 molecules of MTX were bonded to one molecule of the antibody. Further, the volume of the MTX N-hydroxysuccinimide ester solution added to 96.5 antibody (3.0 mg) was changed from 5 μl to 6.5 μl, and through the same operations as in the case of the 5-μl addition, was obtained 2.6 mg of a conjugate in which on average, 6.2 molecules of MTX were linked to 1 molecule of the antibody.

1-4: Determination of the Antigen-Binding Activity (Antibody Activity) of the Conjugates:

The samples to be tested (0.1 ml) of various concentrations are mixed with 0.2 ml of a suspension of human melanoma M14-A cells ($1 \times 10^6$ cells/ml), respectively and the mixtures were intermittently stirred at room temperature for 1 hour to effect the reaction. Then, a constant concentration of 96.5 antibody labeled with $^{125}I$ (abbreviated to $^{125}I$-96.5) was added and the mixtures were occasionally stirred at room temperature to effect the reaction. The cell suspension and the reagent were prepared using phosphate-buffered physiological saline containing 10% normal horse serum and 0.02% sodium azide.

The cells were washed by centrifugation 3 times with 1 ml of the above-stated physiological saline and the radioactivity binding to the cells was determined by means of a gamma-counter.

Thus, the concentration of the conjugate sample at which was conjugate inhibits the binding of $^{125}I$-96.5 to the M14-A cells by 50% ($IC_{50}$) was determined and it is compared with the $IC_{50}$ of the original 96.5 antibody to calculate the antigen-binding activity of the conjugate. As a result, the antigen-binding activity of the conjugate prepared without protection of the amino groups with dimethylmaleic anhydride (described in 1-3) was found to reduce to 29% of the activity of the original antibody, when 4.5 molecules of MTX were bound to 1 molecule of 96.5 antibody on the average and it was found to reduce to 12% of the activity of the original antibody, when 6.2 molecules of MTX were bound to 1 molecule of 96.5 antibody on the average. On the other hand, the antigen-binding activity of the conjugates prepared according to the present invention (described in 1-1) was 100%, when 4.1 to 5.8 molecules of MTX were bound to 1 molecule of the antibody on the average. Thus, the antigen-binding activities of the conjugates prepared according to the present invention were evidently higher than those of conventionally prepared conjugates.

EXAMPLE 2

Instead of 96.5 antibody in EXAMPLE 1, monoclonal antibody ZME019 against human melanoma was used to prepare antibody-MTX conjugates by similar operations as in EXAMPLE 1-1. In other words, 40 μl of a 0.21-M dimethylmaleic anhydride solution in DMF was added to 1.3 ml of 12.7 mg ZME018 a solution in 70 mM borate buffer (pH 8.8) with stirring under cooling with ice-water to effect the reaction for 30 minutes, and the reaction mixture was divided equally into 2 test tubes. One of them was combined with 55 μl of a 30.6-mM MTX N-hydroxysuccinimide ester solution in DMF (the same solution used in EXAMPLE 1-1), while the other was mixed with 83 μl of the solution, then the reactions were effected for 4 hours, respectively. The reaction was stopped by adding 150 μl of a 0.4-M. solution of glycine in 0.1M borate buffer (pH 8.5) to each reaction mixture and stirring the mixture at 4° C. for 1 hour. Then, 70 μl of a 0.1-M hydroxylamine solution (pH 9.0) was added to the reaction mixtures, and they were allowed to stand at 25° C. for 24 hours. The reaction mixtures were subjected to dialysis against 0.02M phosphate buffer 0.14M NaCl (pH 7.2) at 4° C. for 40 hours to remove dimethylmaleyl groups and MTX bound to hydroxyl groups in the antibody to prepare two kinds of the conjugates. The average numbers of MTX molecules bound to 1 molecule of the antibody were determined by the method described in 1-2 and found to be 4.3 and 8.1 in these conjugates, respectively. The antigen-binding activities of these conjugates could be determined using $^{125}I$-labeled ZME018 instead of $^{125}I$-96.5 in EXAMPLE 1-4. The activity was found to be 100% of that of the original antibody, in the conjugate in which 4.3 molecules of MTX were bound to 1 molecule of the antibody on the average, while it was 67% in the conjugate bearing 8.1 molecules of MTX per molecule of antibody on the average. Thus, the present invention gave conjugates with retention of the antigen-binding activity in the case of the ZME018 antibody as in the 96.5 antibody.

Industrial Application

According to the present invention, antibody conjugates with retention of the antigen-binding activity can be prepared effectively and the antibody conjugates may be used over a wide range of applications. For example, a conjugate of a specific antibody with an insoluble support is employed in affinity chromatography, while a conjugate of an antibody with specificity to tumors or thrombosis and a radioactive substance is used in the diagnostic imaging for these tissues. Further, a conjugate of an anti-cancer agent or other cytotoxic substances with an antitumor antibody may be a drug which can act on tumors with high selectivity. Finally, a conjugate of an antibody with a fluorescent substance or an enzyme can be used as a reagent in immunology and biochemistry or as a diagnostic agent.

We claim:

1. A process for making antibody conjugates comprising the steps of:
   (i) protecting a portion of amino groups of said antibody or a fragment thereof, whose antigen-binding capacity is known to be lowered by a convalent modification of amino groups with a compound, with a removable compound to form a modified antibody or fragment thereof comprising an amino group-removable compound complex, wherein said removable compound forms a covalent bond with said antibody;
   (ii) reacting said modified antibody or fragment thereof with a substance that binds to amino groups;
   (iii) treating said modified antibody or fragment thereof to remove the removable compound introduced onto the antibody or fragment thereof by said protecting step (i); and
   (iv) when necessary, removing the substance that is bound to the antibody at functional groups other than amino groups by the binding step (ii).

2. The process of claim 1 wherein the antibody is a monoclonal antibody.

3. The process of claim 1 or claim 2 wherein the removable compound for protein amino groups is a substituted or unsubstituted maleic anhydride.

4. The process of claim 1 or claim 2 wherein the substance that binds to amino groups is a biologically active substance.

5. The process of claim 4 wherein the biologically active substance is cytotoxic or manifests a cytotoxic effect when a second substance facilitates entry of said biologically active substance into cells.

6. The process of claim 5 wherein the substance manifesting a cytotoxic effect is an antitumor substance.

7. The process of claim 1 or claim 2 wherein the substance that binds to amino groups is a chelating agent.

8. The process of claim 1 or claim 2 wherein the substance that binds to amino groups is a compound bearing a carboxyl group that is reactive with amino groups.

* * * * *